United States Patent [19]

Bel et al.

[11] Patent Number: 4,569,333
[45] Date of Patent: Feb. 11, 1986

[54] OPTICAL INSTRUMENT INCLUDING A FOCUSING EYEPIECE AND AN ENDOSCOPE

[75] Inventors: Roger P. Bel, Massy; Martial E. Hascoet, Paris, both of France

[73] Assignee: Metallisations et Traitements Optiques MTO, France

[21] Appl. No.: 494,141

[22] Filed: May 17, 1983

Related U.S. Application Data

[63] Continuation of Ser. No. 269,803, Jun. 3, 1981, abandoned.

[51] Int. Cl.⁴ .............................................. A61B 1/00
[52] U.S. Cl. ........................................................ 128/4
[58] Field of Search ...................................... 128/4–8; 350/96.26, 96.46; 354/286

[56] References Cited

U.S. PATENT DOCUMENTS

| | | | |
|---|---|---|---|
| 2,990,830 | 7/1961 | Hett | 128/4 |
| 3,089,484 | 5/1963 | Hett | 350/96.26 |
| 3,494,353 | 2/1970 | Yokota et al. | 350/76.26 |
| 3,788,303 | 1/1974 | Hall | 128/4 |
| 3,947,088 | 3/1976 | French | 350/96.26 |
| 4,011,017 | 3/1977 | Feverstein et al. | 350/96.26 |
| 4,072,396 | 2/1978 | Ross | 350/46 |
| 4,076,018 | 2/1978 | Heckele | 128/6 |
| 4,141,636 | 2/1979 | Shimojima | 354/196 |
| 4,253,448 | 3/1981 | Terada | 128/6 |

*Primary Examiner*—Edward M. Coven
*Assistant Examiner*—Max F. Hindenburg
*Attorney, Agent, or Firm*—Finnegan, Henderson, Farabow, Garrett & Dunner

[57] ABSTRACT

An optical instrument comprising in the observation device thereof a seal (12) between its cylindrical body (3) and its sleeve (76) as well as sealing coupling means (15, 16, 17, 18) between its body and its first support (4), between the sleeve and the second support (8) and between the lenses (6, 10) and their respective supports; and the observation device and the endoscope (2) are further joined together by complementary assembly means formed by a male member (19) and a female member (20) between which is disposed a seal (21).

5 Claims, 1 Drawing Figure

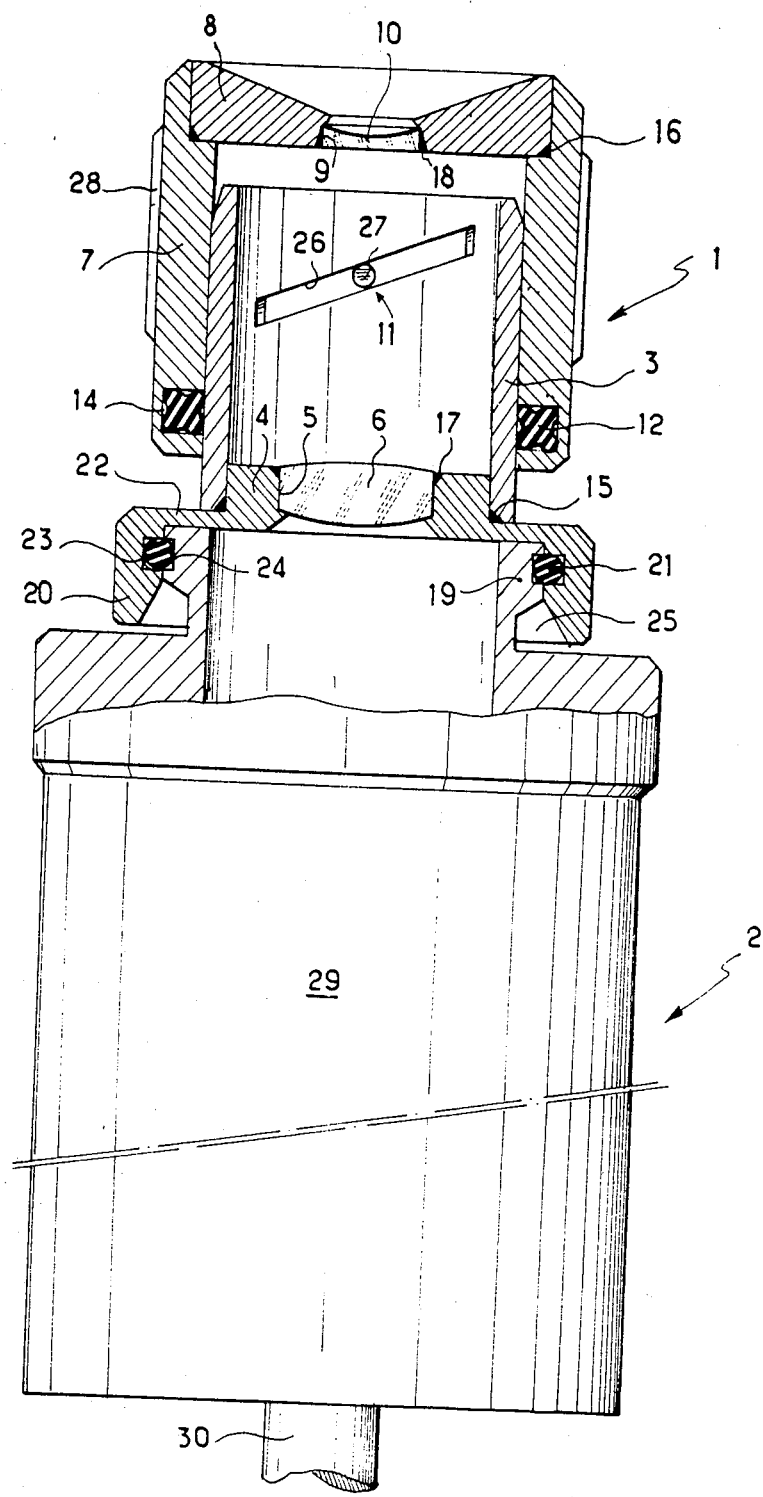

OPTICAL INSTRUMENT INCLUDING A FOCUSING EYEPIECE AND AN ENDOSCOPE

This application is a continuation of application Ser. No. 269,803, filed 6/3/81, now abandoned.

The present invention relates to an optical instrument comprising in combination an observation device, more especially a focussing eye-piece, and an endoscope connected therewith, the observation device comprising a cylindrical body whose end turned towards the endoscope is closed by a first support carrying a first lens, an outer sleeve rotatably mounted on the cylindrical body and whose end the furthest from the endoscope is closed by a second support carrying a second lens, and means for allowing axial movement of the sleeve during rotation thereof.

Endoscopes are at present undergoing considerable development in the medical field where they are used practically systematically when a histological examination or an operation is to be carried out in a cavity of the body of the patient.

In general, these endoscopes are used with an observation device which may be either an eye-piece or a microscope when visual inspection is sufficient or a still or movie camera when it is desired to record the observed image.

For obvious hygienic reasons, the endoscope and the observation device are sterilized before and after each use. Now, at the present time, this treatment is carried out in conditions which are far from being satisfactory. In fact, the endoscope and the observation device are always sterilized independently of each other, which causes the staff a number of handling operations, first of all to separate them with a view to their sterilization, then to re-assemble them once the sterilization has been carried out. Moreover, present observation devices are not perfectly sealed and cannot then be immersed in sterilizing liquids whose use would simplify the sterilization operation and would allow this operation to be carried out with less expensive equipment.

The present invention proposes remedying these drawbacks and, for this, it provides an optical instrument of the above-mentioned type which is characterized in that the observation device comprises a seal between its cylindrical body and its sleeve as well as sealing coupling means between its body and the first support, between the sleeve and the second support and between the lenses and their respective supports; and in that the observation device and the endoscope are further connected to each other by complementary assembly means formed by a male member and a female member between which is disposed a seal.

With the sealing structure of the observation device and with the connection, also sealed, between this latter and the endoscope, the optical instrument of the invention may then be immersed, in the assembled condition, in a sterilizing liquid, which allows considerable reduction in the number of handling operations to be carried out, an appreciable gain in time and the use of simpler and less expensive sterilizing equipment.

When the means provided for axially moving the sleeve are formed by at least one inclined slot formed in the wall of the cylindrical body and into which projects a stud mounted in a through-bore of the wall of the sleeve, it is advantageous for a strip of sealing material to be bonded to the external face of the sleeve and to cover the through-bore of the wall thereof. With such a strip, the seal at the level of the bore may thus be perfectly ensured.

BRIEF DESCRIPTION OF THE DRAWINGS

One embodiment of the present invention will be described hereafter by way of example, which is in no way limiting, with reference to the accompanying drawing in which the single figure is a partial sectional view showing an optical instrument constructed in accordance with the invention.

DETAILED DESCRIPTION OF THE DRAWING

The optical instrument shown in the drawing comprises in combination a focussing eye-piece 1 and a contact endoscope 2 fitted one into the other.

The eye-piece comprises essentially a cylindrical body 3 whose end facing the endoscope is closed by a first support 4 provided with a central bore 5 which is closed by means of a first lens 6, and an outer sleeve 7 rotatably mounted on body 3 and whose end the furthest away from the endoscope is closed by a second support 8 also provided with a central bore 9 closed by means of a second lens 10, and means 11 for moving sleeve 7 axially during rotation thereof and thus contributing to focussing the image from the endoscope, which the user may see by looking through the lens 10.

In accordance with the invention, a seal 12 is provided between body 3 and sleeve 7, this seal being of the "quadring" type, i.e. square in cross-section, and housed in an annular groove of corresponding shape 14 formed in the internal face of the wall of the sleeve.

Annular beads of adhesive 15, 16, 17, and 18 are moreover respectively provided between support 4 and body 3, between support 8 and sleeve 7, between lens 6 and support 4 and between lens 10 and support 8. With the assembly of the different component parts of the eye-piece thus perfectly sealed, this latter may then be immersed in sterilizing liquid without risk.

On the other hand, the eye-piece 1 and endoscope 2 are coupled together by means of a male member 19 and a female member 20 between which is disposed an O-seal 21.

In the example shown, the male member 19 is formed by a cylindrical collar projecting axially from the end of the endoscope which is turned towards the eye-piece. As for the female member 20, it is formed by a cylindrical skirt joined to support 4 and extending coaxially therewith, this skirt being provided at the external periphery of an annular web 22 extending radially with respect to support 4 to which it is joined under the lower end of body 3. As the FIGURE shows, cylindrical skirt 20 includes two portions. One portion located proximate body 3 has one inner diameter. Another portion, located closer to the end of eyepiece 1 to mate with the cylindrical collar of endoscope 2, has an inner diameter which is larger than that of the first portion.

The outer diameter of collar 19 is substantially equal to the inner diameter of the first portion of of skirt 20 so as to provide a relatively tight assembly of the eye-piece and the endoscope.

As can be further seen in the drawing, the O-seal 21 is housed in an annular groove 23, of a depth less than the diameter of the seal, formed in the internal face of the skirt. The O-seal 21, which thus projects slightly, cooperates with a shallow groove 24 provided on the collar 19 to ensure coupling between the eye-piece and the endoscope. The seal is situated slightly above an annular chamber 25 provided between the free end of the skirt and the root of the collar, this chamber forming a leakage trap.

Of course, seal 21 and chamber 25 seal off perfectly the connection formed between the eye-piece and the endoscope, which allows then these two elements to be immersed, in the assembled condition, in a sterilizing liquid.

It will also be noted that the means 11 for axially moving the sleeve are formed by an inclined slot 26 formed in the wall of body 3 as well as by a stud 27 carried by the internal face of the sleeve and projecting into slot 26. In the example shown, stud 27 is mounted in a through-bore in the wall of the sleeve. To prevent the sterilizing liquid from penetrating into the eye-piece through this bore, a strip of sealing material 28 is advantageously bonded to the external face of the sleeve so as to cover said bore.

It should finally be noted that the contact endoscope 2 here comprises a sleeve 29 and a guide 30 which are quite conventional. It is then pointless to describe here the structure of these two parts.

The present invention is in no way limited to the optical instrument which has just been described with reference to the drawing. It covers in fact any optical instrument which might be formed by the combination of a contact endoscope or ordinary endoscope with an observation device such as a microscope, a still or cine camera, provided of course that this optical instrument presents the characteristics and technical advantages outlined above.

We claim:

1. An optical instrument comprising, in combination, a focusing eyepiece and an endoscope coupled therewith, the eyepiece comprising:

a cylindrical body, a first support carrying a first lens sealed to one end of the cylindrical body nearest the endoscope, an external sleeve rotatably and slidably mounted on the cylindrical body so as to surround said body, said sleeve having a second support carrying a second lens which is in axial alignment with the first lens and being sealed to one end of the sleeve so that the sleeve and the second support form a cap that closes off the open end of the cylindrical body furthest from the endoscope, means for causing sliding axial movement of the sleeve relative to the cylindrical body during rotation of the sleeve thereby to adjust the relative spacing between the first and second lenses for focusing said instrument, an annular seal located between the cylindrical body and the sleeve that permits the sleeve to rotate and slide axially relative to the cylindrical body while maintaining a sealing relationship between them, and a complementary assembly means for coupling the eyepiece and the endoscope together, said complementary assembly means comprising a cylindrical skirt that extends radially outward from the first support and co-axially with the endoscope and containing a first portion having a first inner diameter and a second portion, aligned with said first portion, and having a second inner diameter larger than said first inner diameter and being located closer to the end of the eyepiece to be coupled to the endoscope than said first portion, said skirt mating with a cylindrical collar projecting outwardly from the end of the endoscope to be coupled to the eyepiece, the outer diameter of the cylindrical collar being substantially equal to the inner diameter of the skirt to provide a relatively tight fit with a resilient annular seal between the collar and the skirt that allows separation of the eyepiece and the endoscope only by relative axial movement between them while maintaining a sealing relationship between them when they are coupled together.

2. The optical instrument of claim 1 in which the annular seal between the cylindrical body and the sleeve is square in cross section and is housed in an annular groove of corresponding shape formed in the internal face of the wall of the sleeve.

3. The optical instrument of claim 1 wherein the outer end of the collar of the endoscope bears against the first support of the eyepiece when the endoscope is assembled to the eyepiece.

4. The optical instrument of claim 1 wherein the annular seal between the collar and the skirt is an O-seal housed in an annular groove formed in the inner diameter of the skirt and projecting inwardly therefrom into a groove on the outer diameter of the collar.

5. The optical instrument of claim 1 in which the means for axially moving the sleeve as it is rotated comprises an inclined slot formed in the wall of the cylindrical body into which projects a stud mounted in a bore in the wall of the sleeve and a strip of sealing material bonded to the external face of the sleeve to cover and seal the bore in the wall of the sleeve.

* * * * *